(12) United States Patent
Monro

(10) Patent No.: US 7,750,299 B2
(45) Date of Patent: Jul. 6, 2010

(54) ACTIVE BIOMETRIC SPECTROSCOPY

(76) Inventor: Donald Martin Monro, 6, The Lays, Goose Street, Beckington, Somerset BA11 6RS (GB)

( * ) Notice: Subject to any disclaimer, the term of this patent is extended or adjusted under 35 U.S.C. 154(b) by 530 days.

(21) Appl. No.: 11/470,609

(22) Filed: Sep. 6, 2006

(65) Prior Publication Data

US 2008/0058619 A1  Mar. 6, 2008

(51) Int. Cl.
  *G01J 1/00* (2006.01)
(52) U.S. Cl. .................... 250/336.1; 356/300
(58) Field of Classification Search ................. 382/115; 356/300; 250/336.1
  See application file for complete search history.

(56) References Cited

U.S. PATENT DOCUMENTS

| | | | |
|---|---|---|---|
| 4,484,317 A * | 11/1984 | Anderson | 367/150 |
| 5,365,237 A | 11/1994 | Johnson et al. | |
| 5,539,207 A | 7/1996 | Wong | |
| 5,910,999 A | 6/1999 | Mukohzaka | |
| 6,353,244 B1 | 3/2002 | Yamazaki et al. | |
| 6,703,596 B1 | 3/2004 | Moran | |
| 6,747,736 B2 | 6/2004 | Takahashi | |
| 6,777,684 B1 | 8/2004 | Volkov et al. | |
| 6,816,605 B2 | 11/2004 | Rowe et al. | |
| 6,870,619 B1 | 3/2005 | Tenhunen et al. | |
| 7,019,682 B1 | 3/2006 | Louberg et al. | |
| 7,124,043 B2 | 10/2006 | Stein et al. | |
| 7,147,153 B2 | 12/2006 | Rowe et al. | |
| 7,172,563 B2 | 2/2007 | Takiguchi et al. | |
| 2003/0223621 A1 * | 12/2003 | Rowe et al. | 382/115 |
| 2004/0081020 A1 * | 4/2004 | Blosser et al. | 367/96 |
| 2004/0240712 A1 | 12/2004 | Rowe et al. | |
| 2005/0043630 A1 | 2/2005 | Buchert | |
| 2005/0049877 A1 | 3/2005 | Agranat | |
| 2005/0192516 A1 | 9/2005 | Takiguchi et al. | |
| 2005/0092191 A1 | 10/2005 | Canon et al. | |
| 2006/0054824 A1 * | 3/2006 | Federici et al. | 250/339.02 |
| 2006/0097176 A1 | 5/2006 | Szu | |
| 2006/0128311 A1 | 6/2006 | Tesfai | |
| 2006/0255277 A1 * | 11/2006 | Cole et al. | 250/341.1 |
| 2006/0273255 A1 | 12/2006 | Volkov et al. | |
| 2007/0029483 A1 | 2/2007 | James et al. | |
| 2007/0030115 A1 * | 2/2007 | Itsuji et al. | 340/5.8 |
| 2007/0210956 A1 | 9/2007 | Hillis et al. | |
| 2007/0237365 A1 | 10/2007 | Monro | |
| 2007/0262257 A1 | 11/2007 | Monro | |
| 2007/0290800 A1 * | 12/2007 | Fuller | 382/115 |

(Continued)

FOREIGN PATENT DOCUMENTS

CA  2539040 A1  3/2005

(Continued)

OTHER PUBLICATIONS

Globus et al., "Submillimeter-wave Fourier transform spectroscopy of biological macromolecules," Journal of Applied Physics, vol. 91 No. 9, May 1, 2002, pp. 6105-6115.

(Continued)

*Primary Examiner*—Kara E Geisel
(74) *Attorney, Agent, or Firm*—Sterne, Kessler, Goldstein & Fox P.L.L.C.

(57) ABSTRACT

Embodiments of methods, apparatuses, systems and/or devices for active biometric spectroscopy are disclosed.

26 Claims, 2 Drawing Sheets

Biometric Spectroscopy

U.S. PATENT DOCUMENTS

| | | | |
|---|---|---|---|
| 2008/0014580 A1* | 1/2008 | Alfano et al. | 435/6 |
| 2008/0097183 A1 | 4/2008 | Monro | |
| 2008/0161674 A1* | 7/2008 | Monro | 600/410 |
| 2008/0228083 A1* | 9/2008 | Wu et al. | 600/475 |

FOREIGN PATENT DOCUMENTS

| | | |
|---|---|---|
| DE | 101 53 407 A1 | 2/2003 |
| EP | 1 868 005 A | 12/2007 |
| GB | 1 488 712 A | 10/1977 |
| GB | 2 311 368 A | 9/1997 |
| JP | 2004 265353 A | 9/2004 |
| JP | 60 098335 A | 2/2005 |
| JP | 2005 172775 A | 6/2005 |
| RO | 70 605 A2 | 5/1982 |
| RU | 2 066 117 C1 | 9/1996 |
| UA | 78 022 C | 2/2007 |
| WO | WO96/17546 A | 6/1996 |
| WO | WO01/48681 A2 | 7/2001 |
| WO | WO02/084605 | 10/2002 |
| WO | WO03/031954 | 4/2003 |
| WO | WO03/031954 A1 | 4/2003 |
| WO | WO2004/086939 | 10/2004 |
| WO | WO2005/026833 A2 | 3/2005 |
| WO | WO2005/092191 A2 | 10/2005 |
| WO | WO2005/119581 | 12/2005 |
| WO | WO2006/082550 | 8/2006 |
| WO | WO2007/118219 | 10/2007 |
| WO | WO2008/013704 | 1/2008 |
| WO | WO2008/030425 | 3/2008 |
| WO | WO2008/030427 | 3/2008 |

OTHER PUBLICATIONS

Chandra Sekharan P., "Identification of Skull from its Suture Pattern," Forensic Science International, Mar. 1985, vol. 27, No. 3, pp. 205-214.

Globus et al., "Terahertz Fourier transform characterization of biological materials in a liquid phase," Journal of Physics D. Applied Physics, Institute of Physics Publishing, Bristol, GB, vol. 39, No. 15, Aug. 7, 2006, pp. 3405-3413.

Woolard D. L. et al, "Millimeter Wave-Induced Vibrational Modes in DNA as a Possible Alternative to Animal Tests to Proble for Carcinogenic Mutations," Journal of Applied Toxicology, Wiley Heyden LTD, GB, vol. 17, No. 4, Aug. 1997, pp. 243-246.

Database WPI Week 200547, Derwent Publications Ltd., London, GB; AN 2005-462389 & JP 2005-172775 (ZH Handotai Kenkyu Shinkokai) Jun. 30, 2005.

International Search Report for Appln. No. PCT/US2007/066191 issued Dec. 27, 2007, 5 pages.

International Search Report for Appln. No. PCT/US2007/016229 issued Mar. 13, 2008, 3 pages.

International Search Report for Appln. No. PCT/US2007/019296 issued Mar. 20, 2008, 6 pages.

International Search Report for Appln. No. PCT/US2007/019298 issued Mar. 20, 2008, 7 pages.

Non-Final Office Action for U.S. Appl. No. 11/433,073, mailed Mar. 10, 2008, 11 pages.

Written Opinion for Appln. No. PCT/US2007/019298 issued Mar. 20, 2008, 9 pages.

Jing, "Millimeter Wave Absorption Spectroscopy of Biological Polymers" PhD Thesis, Stevens Institute of Technology, 92 pgs., 2001.

Van Zandt et al., Millimeter-Microwave Spectrum of DNA: Six Predictions for Spectroscopy, Phys. Rev. A, vol. 39, Issue 5, pp. 2672-2674, Mar. 1, 1989.

Final Office Action for U.S. Appl. No. 11/433,073, mailed Jul. 24, 2008, 12 pages.

International Search Report for Appln. No. PCT/US2007/026127, issued Jun. 30, 2008, 13 pages.

Written Opinion for Appln. No. PCT/US2007/066191 issued Oct. 7, 2008, 5 pages.

Non-Final Office Action for U.S. Appl. No. 11/399,752, mailed Aug. 25, 2009, 11 pages.

Non-Final Office Action for U.S. Appl. No. 11/399,752, mailed Jan. 14, 2010, 11 pages.

Non-Final Office Action for U.S. Appl. No. 11/470,615, mailed Jun. 19, 2009, 15 pages.

Final Office Action for U.S. Appl. No. 11/470,615, mailed Jan. 5, 2010, 13 pages.

Donald Monro, U.S. Appl. No. 11/618,613 entitled "Active InVivo Spectroscopy," filed Dec. 29, 2006.

Donald Monro, U.S. Appl. No. 11/470,615 entitled "Passive InVivo Substance Spectroscopy," filed Sep. 6, 2006.

Donald Monro, PCT Serial No. PCT/US2007/008864, entitled "Biometric Identification," filed Apr. 9, 2007.

Donald Monro, PCT Serial No. PCT/US2007/016229, entitled "Passive Biometric Spectroscopy," filed May 11, 2007.

Donald Monro, PCT Serial No. PCT/US2007/019298, entitled "Passive InVivo Substance Spectroscopy," filed Sep. 5, 2007.

Donald Monro, PCT Serial No. PCT/US2007/019296, entitled "Active Biometric Spectroscopy," filed Sep. 5, 2007.

Donald Monro, PCT Serial No. PCT/US2007/026127, entitled "Active InVivo Spectroscopy," filed Dec. 21, 2007.

Donald Monro, PCT Serial No. PCT/US2007/066191, entitled "Biometric Identification," filed Apr. 9, 2007.

Globus et al., "Submillimeter-wave Fourier transform spectroscopy of biological macromolecules," Journal of Applied Physics, vol. 91 No. 9, May 1, 2002, pp. 6105-6115.

* cited by examiner

Absorption features of Herring DNA film at normal incidence

Absorption features of Salmon DNA film at normal incidence

Biometric Spectroscopy

ACTIVE BIOMETRIC SPECTROSCOPY

FIELD

This disclosure is related to active biometric spectroscopy.

BACKGROUND

In a variety of contexts, having the ability to perform biometric spectroscopy may be desirable.

BRIEF DESCRIPTION OF THE DRAWINGS

Subject matter is particularly pointed out and distinctly claimed in the concluding portion of the specification. Claimed subject matter, however, both as to organization and method of operation, together with objects, features, and advantages thereof, may best be understood by reference of the following detailed description if read with the accompanying drawings in which:

DETAILED DESCRIPTION

Figure 1:
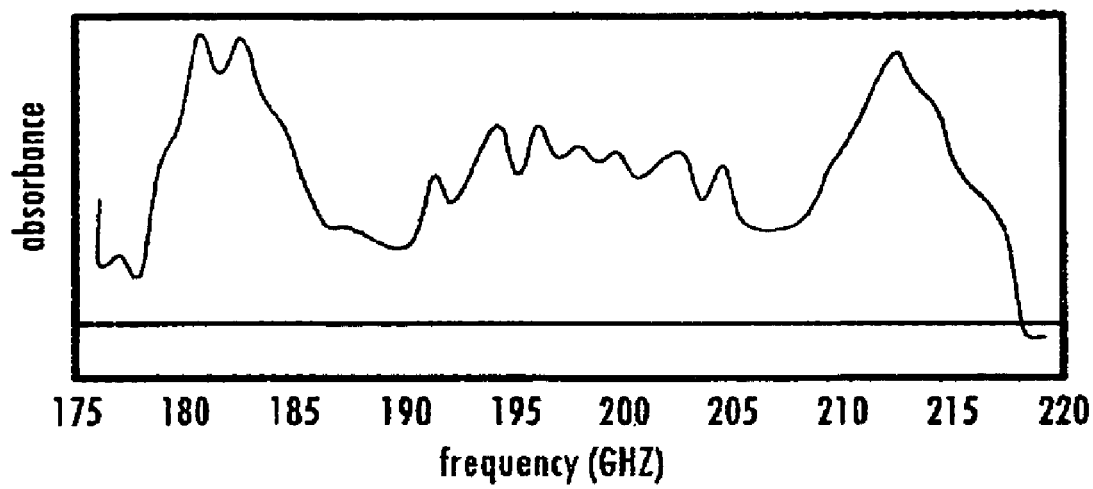
FIG. 1 is a plot illustrating the absorption features of Herring DNA.

In the following detailed description, numerous specific details are set forth to provide a thorough understanding of claimed subject matter. However, it will be understood by those skilled in the art that claimed subject matter may be practiced without these specific details. In other instances, well-known methods, procedures, components and/or circuits have not been described in detail so as not to obscure claimed subject matter.

Some portions of the detailed description which follow are presented in terms of algorithms and/or symbolic representations of operations on data bits and/or binary digital signals stored within a computing system, such as within a computer and/or computing system memory. These algorithmic descriptions and/or representations are the techniques used by those of ordinary skill in the data processing arts to convey the substance of their work to others skilled in the art. An algorithm is here, and generally, considered to be a self-consistent sequence of operations and/or similar processing leading to a desired result. The operations and/or processing may involve physical manipulations of physical quantities. Typically, although not necessarily, these quantities may take the form of electrical and/or magnetic signals capable of being stored, transferred, combined, compared and/or otherwise manipulated. It has proven convenient, at times, principally for reasons of common usage, to refer to these signals as bits, data, values, elements, symbols, characters, terms, numbers, numerals and/or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing", "computing", "calculating", "determining" and/or the like refer to the actions and/or processes of a computing platform, such as a computer or a similar electronic computing device, that manipulates and/or transforms data represented as physical electronic and/or magnetic quantities and/or other physical quantities within the computing platform's processors, memories, registers, and/or other information storage, transmission, and/or display devices.

In this context, biometrics refers to methods of identifying or characterising members of a species by measuring data in a form known to vary between members of the species capable to a greater or lesser extent of distinguishing between members of the species for identification purposes. In this context, therefore, the term biometric spectroscopy refers to the use of active signal emissions to distinguish between or identify members of a species for identification purposes, such as between animals or humans, for example. It is noted that a variety of signals may be employed and claimed subject matter is not limited to a particular type of signal emission. To provide some examples, electromagnetic signals and/or ultrasound signals may be employed.

As is well-known, each human has a unique DNA. Despite its simple sequence of bases, the DNA molecule, in effect, codes all aspects of a particular species' characteristics. Furthermore, for each individual, it codes all the unique distinguishing biological characteristics of that individual. The DNA of an individual is also inherited at least partly from each biological parent and may be used to identify the individual or their ancestry. Work has gone on for many years, and is continuing, to relate particular DNA sequences to characteristics of a person having that DNA sequence. Thus, the DNA of an individual may reveal the genes inherited by an individual and may also, in some cases, reveal an abnormality or predisposition to certain inherited diseases, for example.

From the fields of chemistry and physics, atoms and molecules are known to provide a unique response if exposed to electromagnetic radiation, such as radio waves and/or light, for example. At the atomic or molecular level, radiation may be absorbed, reflected, or emitted by the particular atom or molecule. This produces a unique signature, although which of these phenomena take place may vary depending at least in part upon the particular frequency of the radiation impinging upon the particular atom or molecule.

Figure 2:
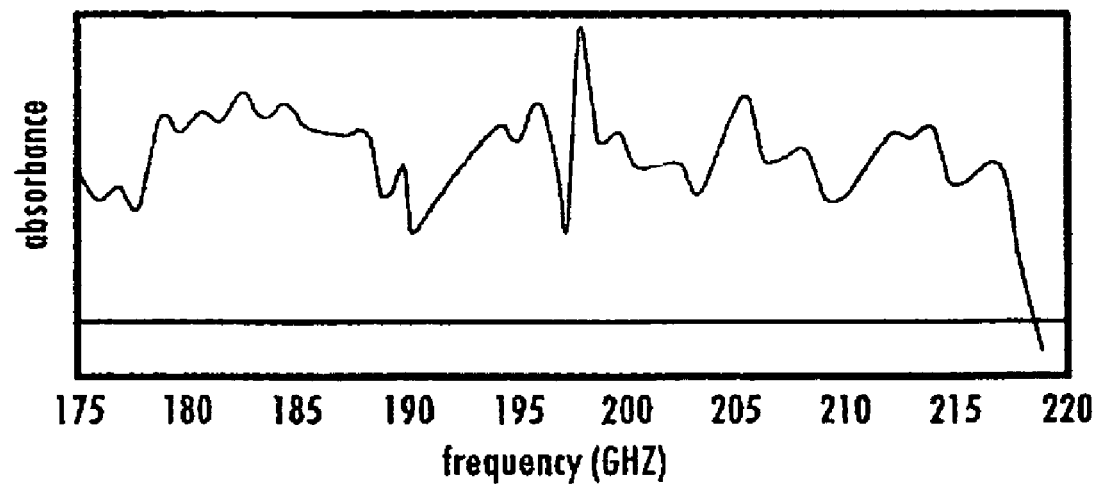
FIG. 2 is a plot illustrating the absorption features of Salmon DNA.

Experiments have shown that species may be distinguished by their absorption spectrum in millimeter electromagnetic waves. See Jing Ju, "Millimeter Wave Absorption Spectroscopy of Biological Polymers," PhD Thesis, Stevens Institute of Technology, Hoboken, N.J., 2001. For example, FIGS. 1 and 2 illustrate absorption features of Herring and Salmon DNA, respectively. An approach, although claimed subject matter is not limited in scope in this respect, may include applying or observing a range of millimeter wavelengths and recording the spectral response to those millimeter wavelengths at a receiver. In such an approach, peaks and troughs in the spectral response may provide a spectrum or signature for comparison.

Therefore, waves applied to an object may be absorbed, scattered and/or reflected by the sample or the object of the radiation and the reflected, transmitted and/or scattered waves may be detected and/or recorded. At certain frequencies, modes of vibration of molecules or atoms in a sample result in radiation at that frequency being more highly absorbed, scattered or reflected compared to waves at other frequencies. At some frequencies, the sample may even emit more energy than it receives by a process that transfers energy to a resonant mode of vibration from an absorptive one.

Electromagnetic and/or mechanical resonances may be observed. In a spectral plot, this process or phenomenon may result in peaks and troughs producing a identifiable signature.

In particular, in phonon resonance, molecules or portions of them may vibrate mechanically at frequencies, such as those of interest. It is well-known by the relation $$v = f*l \text{ i.e. } l = v/f$$

where v is the velocity of propagation of the wave, f is its frequency and l is the wavelength, that the wavelength is shorter for a wave that propagates more slowly. As such vibrations here are mechanical, it may be possible to induce them mechanically with sound waves of substantially the same frequency but much shorter wavelengths, e.g., ultrasound. A possible disadvantage of ultrasound is that it cannot easily be applied via free space unlike electromagnetic waves; however to induce a particular frequency of vibration the wavelength may be much shorter. This would therefore enable the use of frequencies shorter than for electromagnetic waves.

In one embodiment, actively emitted waves in the appropriate range may be observed as absorbing and/or emitting resonances in the molecules and structures they encounter as they pass through a body to which they may be directed. For example, for such an embodiment, radiation may be applied over a broad range of frequencies, e.g., spread spectrum, and a receiver may sweep through the spectrum to determine the strength or intensity of received radiation over a suitably narrow bandwidth. In another embodiment, a receiver may instead be sensitive over a broad range of frequencies and radiation applied may be swept through the spectrum. In a third embodiment, applied and received frequencies may be swept in synchrony, although one or the other could have a narrower bandwidth to provide frequency resolution. Thus, a suitably sensitive receiver may be constructed so as to scan a suitable range of frequencies. Such a receiver may therefore detect and likewise may be employed to produce a spectrographic pattern which is characteristic of the structures and/or molecules that encountered the radiation.

Due at least in part to differences in molecular structure, different DNA will produce different spectrographic patterns at the receiver. Therefore, individuals, for example, may be differentiated by a signature spectrum, such as, for example, peaks and troughs in the spectrum, of actively emitted radiation over a suitable range of frequencies.

In one embodiment, for example, measurement may be accomplished via transmission. It might seem that as frequencies are swept, complex and changing patterns of reflection and scattering from internal structures, such as bone, muscle, cartilage and so on, particularly at frequencies that for some embodiments may comprise very short wavelengths, might obscure the spectrum sought. Partly this may be mitigated by choosing suitable sites for measurement, such as an earlobe, pinna or other relatively homogenous part of an anatomy. However, it is also noted that these changes should occur more slowly than peaks and troughs in the spectrum that are of interest. Thus, high pass filtering a swept receiver signal may address wide peaks and troughs due to large anatomical structures while preserving sharper peaks and troughs arising from resonances and emissions of molecules. Likewise, focusing radiation using a reflector, as shown in FIG. 3, or by some other method may be employed and may help to reduce or reject unwanted resonances by directing applied waves more precisely and/or restrict analysis to waves emanating from a desired region.

Figure 3:
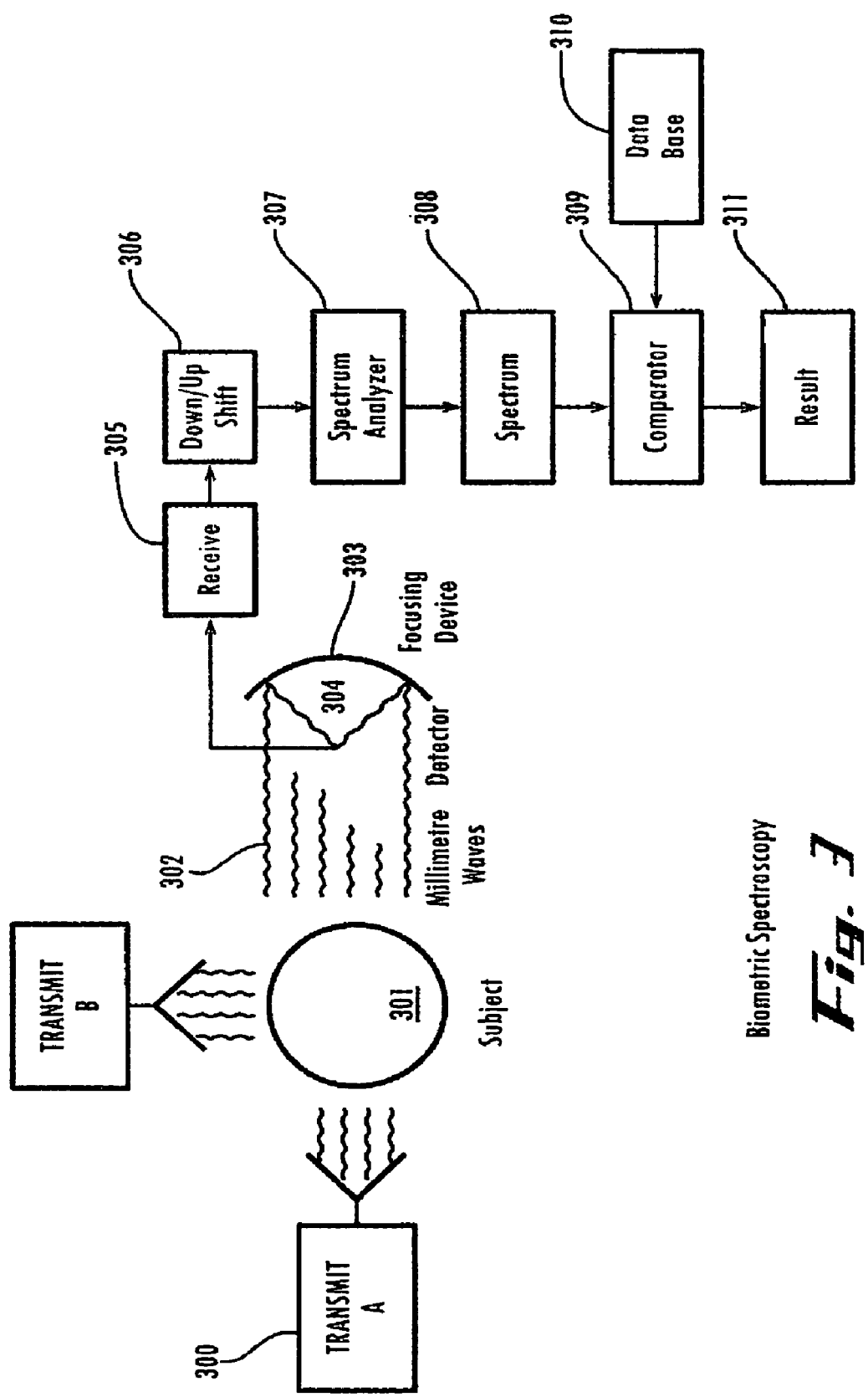
FIG. 3 is a schematic diagram illustrating one embodiment of an apparatus for active biometric spectroscopy.

Referring to FIG. 3, for example, waves may be applied by an apparatus, such as a transmitter 300. In this particular embodiment, the waves may be modified by interaction with subject 301 to give transmitted, scattered and/or reflected waves 302 which may be focused by a focusing device 305 onto a detector 304. The reflected waves may be the result of a transmitter directing signals at an object of interest. It is noted, of course, that for this embodiment, signals are not limited to electromagnetic signals and may include other types of signals such as ultrasound and/or optical signals, for example. Signals from detector 304 may be passed to a receiver 305 which may amplify the signals before down-shifting or up-shifting the signals, at 306, to a frequency range convenient for spectrum analyzer 307. Of course, 306 may also be omitted for some embodiments. Spectrum analyzer 307 may operate in a particular frequency range, whichever may be convenient for the frequency range of interest. Resulting spectrum 308 may be compared, at 309, with previously stored spectrograms, such as, in this example, from a database 310, to produce a result 311 indicative of the quality of the match between spectrum 308 for subject 301 and spectra from database 310. Of course, this is merely one example embodiment provided for purposes of illustration. Many other embodiments are possible and are included within the scope of claimed subject matter.

It is possible that any of the frequencies mentioned above might be used and claimed subject matter is intended to cover such frequencies mentioned; however, one range to be employed, for example, may be from approximately 10 GHz to approximately 1 THz for electromagnetic signals, although, again, claimed subject matter is not limited in scope in this respect. Of course, it is difficult to predict how developments in technology may affect or influence an appropriate frequency range for use in such an application. Nonetheless, this interestingly corresponds with a prediction made by Van Zandt and Saxena in 1988, that some DNA molecules may be expected to exhibit resonances in approximately this range. See Van Zandt and Saxena, "Millimeter-microwave spectrum of DNA: Six predictions for Spectroscopy," Phys. Rev. A 39, No. 5, pp 2692-2674, March, 1989. Likewise, a recent finding by Jing Ju indicates DNA from various species of fish and bacteria may be differentiated by millimeter wave spectroscopy in the range of approximately 180 to approximately 220 GHz. See Jing Ju, "Millimeter Wave Absorption Spectroscopy of Biological Polymers," PhD Thesis, Stevens Institute of Technology, Hoboken, N.J., 2001.

It is noted that in some situations the emissions of interest may be of relatively low power or intensity level, so that long measurements may be desirable to obtain sufficient quanta to get a reasonable resolution of the spectrogram. In such situations, it may also be desirable to take steps to reduce measurement time. Any one of a number of techniques may be employed if this is desired. For example, one approach may be to place the individual in a suitable environment in which the background emits the radiation of a cold body. In another approach, radiation may be focused on a detector to increase its intensity, including large reflectors that at least partly or wholly surround the subject. Likewise, both approaches may be employed in some embodiments, if desired. In yet another approach, measurement time may be reduced by employing multiple receivers. For example, in one such embodiment, different receivers may be employed to cover different parts of the spectrum, such as a case in which some receivers are optical receivers and others are radio receivers, although, of course, claimed subject matter is not limited in scope in this respect. Likewise, in some embodiments, different types of signals may be used in combination, such as electromagnetic and ultrasound signals, for example.

Likewise, a variety of spectrographic and detection techniques could be employed. In one embodiment, radio waves could be sampled and Analog-to-Digital (A/D) conversion may be employed, either directly at lower frequencies, or after modulation by a suitable carrier for down conversion to lower frequencies. In this embodiment, spectral analysis may be accomplished by applying well-known Fast Fourier Transform (FFT) techniques, for example. In such an embodiment, sampling rate and sampling duration are parameters that may affect bandwidth and line width, respectively.

In another embodiment, the frequency of the waves may be modulated upwards, for example, in one example, by an optical carrier into the optical or infra-red range and spectral analysis may be accomplished through application of standard optical spectrographic techniques, such as application of prism or prism-like technology so that light of different frequencies may be focused to detectors corresponding to a particular light frequency.

Frequencies characteristic of an individual may also be related to characteristics that differentiate the absorption or radiation characteristics of an individual, in addition to or instead of DNA resonances, depending on the particular embodiment, for example. Therefore, the range of frequencies to be employed may vary. Furthermore, claimed subject matter is not limited in scope to a particular range, of course.

As is well-known, a biometric system may be applied to identify a candidate individual from a large population, referred to in this context as one to many matching, or to verify that an candidate individual is the individual claimed with a reasonable degree of confidence, referred to in this contact as one to one matching. Nonetheless, the foregoing is not intended to limit potential biometric applications. Therefore, these applications, as well as others, are intended to be included within the scope of claimed subject matter. For example, biometrics may be applied for identification in connection with humans as well as applied to other species.

Identification of "individuals" in any species is a task with multiple potential applications. For example, for animal species that provide a source of meat, it may be desirable to track the sale and movement of individual animals for health purposes. Likewise, in other instances, tracking individual animals, such as horses or dogs, for example, may be desirable to reduce fraud and/or theft. In general, active spectroscopy, such as employing electromagnetic radiation, for example, may provide the ability to track movement of individual animals in a non-invasive and highly specific, yet relatively safe manner.

In an example, there is a method including actively applying radiation to a selected species, measuring radiation in the vicinity of the selected species over a range of frequencies to obtain a frequency spectrum, and comparing the obtained frequency spectrum to one or more frequency spectra signatures. Optionally, the method includes identifying the frequency spectrum of the one or more frequency spectra that most closely resembles the obtained frequency spectrum. The method can be used where the selected species is a human. The identifying the one or more frequency spectra that most closely resemble the obtained frequency spectrum can distinguish between different species. Further, the identifying the one or more frequency spectra that most closely resemble the obtained frequency spectrum can distinguish between different specimens of the same species, including the human species. The radiation can include electromagnetic radiation that falls in the range from approximately 10 GHz to approximately 1 THz. The radiation can include electromagnetic radiation that is measured for a sufficiently long period of time to obtain sufficient energy to produce a spectrogram. The radiation can be actively applied by focusing the radiation. The radiation can be measured by focusing the radiation. Optionally, the radiation is measured by employing multiple detectors. Different detectors cover a different range of frequencies.

In an example, there is an apparatus including a transmitter to actively apply electromagnetic radiation to a selected species, a detector to measure electromagnetic radiation in the vicinity of a species in a range of frequencies, and a computing platform adapted to produce a spectrogram from the detector measurements as well as to compare the spectrogram against other spectra to be stored on the computing platform. The transmitter can include a mechanism to focus the electromagnetic radiation for measurement. Further, the detector can include a mechanism to focus the electromagnetic radiation for measurement. The computing platform can include an A/D converter and is capable of implementing an FFT. The computing platform to produce the spectrogram can be adapted to shift the range of frequencies for spectrum analysis.

In an example, there is an apparatus including means for actively applying radiation to a selected species, means for measuring radiation in the vicinity of a species over a range of frequencies to obtain a frequency spectrum, and means for comparing the obtained frequency spectrum to one or more frequency spectra signatures. Optionally, the apparatus includes means for identifying the frequency spectrum of the one or more frequency spectra that most closely resembles the obtained frequency spectrum. The means for identifying the one or more frequency spectra that most closely resemble the obtained frequency spectrum can include means for distinguishing between different species. The means for identifying the one or more frequency spectra that most closely resemble the obtained frequency spectrum can include means for distinguishing between different specimens of the same species. The species can include the human species. The radiation can include electromagnetic radiation that falls in the range from approximately 10 GHz to approximately 1 THz.

In an example, there is an article including a storage medium having stored thereon instructions that, if executed, result in execution of the following method by a computing platform: actively measuring radiation in the vicinity of a species over a range of frequencies to obtain a frequency spectrum and comparing the obtained frequency spectrum to one or more frequency spectra signatures. Optionally, the storage medium comprises instructions that, if executed, further results in identifying the frequency spectrum of the one or more frequency spectra that most closely resembles the obtained frequency spectrum. The storage medium can include instructions that, if executed, further results in identifying the one or more frequency spectra that most closely resemble the obtained frequency spectrum distinguishes between different species. Further, the storage medium can include instructions that, if executed, further results in identifying the one or more frequency spectra that most closely resemble the obtained frequency spectrum distinguishes between different specimens of the same species. The storage medium can include instructions that, if executed, further results in radiation being measured for a sufficiently long period of time to obtain sufficient quanta to produce a spectrogram.

It will, of course, be understood that, although particular embodiments have just been described, claimed subject matter is not limited in scope to a particular embodiment or implementation. For example, one embodiment may be in hardware, such as implemented to operate on a device or combination of devices, for example, whereas another embodiment may be in software. Likewise, an embodiment may be implemented in firmware, or as any combination of hardware, software, and/or firmware, for example. Likewise, although claimed subject matter is not limited in scope in this respect, one embodiment may comprise one or more articles, such as a storage medium or storage media. This storage media, such as, one or more CD-ROMs and/or disks, for example, may have stored thereon instructions, that if executed by a system, such as a computer system, computing platform, or other system, for example, may result in an embodiment of a method in accordance with claimed subject matter being executed, such as one of the embodiments previously described, for example. As one potential example, a computing platform may include one or more processing units or processors, one or more input/output devices, such as a display, a keyboard and/or a mouse, and/or one or more memories, such as static random access memory, dynamic random access memory, flash memory, and/or a hard drive.

In the preceding description, various aspects of claimed subject matter have been described. For purposes of explanation, specific numbers, systems and/or configurations were set forth to provide a thorough understanding of claimed subject matter. However, it should be apparent to one skilled in the art having the benefit of this disclosure that claimed subject matter may be practiced without the specific details. In other instances, well known features were omitted and/or simplified so as not to obscure claimed subject matter. While certain features have been illustrated and/or described herein, many modifications, substitutions, changes and/or equivalents will now occur to those skilled in the art. It is, therefore, to be understood that the appended claims are intended to cover all such modifications and/or changes as fall within the true spirit of claimed subject matter.

The invention claimed is:

1. A method, comprising:
    applying electromagnetic radiation to at least partially penetrate an organism using a source of the electromagnetic radiation spaced from the organism;
    measuring radiation proximate to the organism over a range of frequencies to obtain a measured spectrum;
    comparing the measured spectrum to a frequency spectra signature to generate a comparison result; and
    producing a spectrogram from the measured spectrum.

2. The method of claim 1, further comprising:
    comparing the measured spectrum to a second frequency spectra signature to generate a second comparison result; and
    determining which of the frequency spectra signature and the second frequency spectra signature most closely resembles the measured spectrum.

3. The method of claim 1, wherein the applying radiation further comprises using a human as the organism.

4. The method of claim 1, further comprising:
    using the comparison result to distinguish between the organism and a second organism.

5. The method of claim 1, further comprising:
    applying second radiation to a second organism;
    measuring second radiation proximate to the second organism over a second range of frequencies to obtain a second measured spectrum;
    comparing the second measured spectrum to a second frequency spectra signature to determine a second comparison result; and
    using the comparison result and the second comparison result to distinguish the organism from the second organism.

6. The method of claim 1, wherein the applying radiation further comprises focusing the radiation on the organism.

7. The method of claim 1, wherein the measuring radiation further comprises focusing the radiation on a detector.

8. The method of claim 1, wherein the measuring radiation further comprises measuring the radiation with a plurality of detectors.

9. The method of claim 1, wherein the measuring radiation further comprises using detectors that each measure a different frequency range in the plurality of detectors.

10. An apparatus, comprising:
    a transmitter configured to apply electromagnetic radiation to at least partially penetrate an organism, wherein the transmitter is spaced from the organism;
    a detector located proximate to the organism and configured to measure radiation that has interacted with the organism;
    an apparatus configured to focus the radiation after it has interacted with the organism onto the detector; and
    an analyzer coupled to the detector and the transmitter,
    wherein the analyzer is configured to produce a measured spectrum from a detector measurement over a range of frequencies and to compare the measured spectrum to a frequency spectra signature to determine a comparison result, and
    wherein the analyzer is configured to produce a spectrogram from the measured spectrum.

11. The apparatus of claim 10, wherein the analyzer is configured to implement a fast Fourier transform to produce the spectrogram.

12. The apparatus of claim 10, wherein the analyzer is configured to shift the range of frequencies to produce the spectrogram.

13. The apparatus of claim 10, wherein the analyzer is further configured to:
    compare the measured spectrum to a second frequency spectra signature to determine a second comparison result; and
    determine which of the frequency spectra signature and the second frequency spectra signature most closely resembles the measured spectrum.

14. The apparatus of claim 10, wherein the organism comprises a human organism.

15. The apparatus of claim 10, wherein the analyzer is configured to use the comparison result to distinguish the organism from a second organism.

16. The apparatus of claim 10, wherein:
    the transmitter is configured to apply second radiation to a second organism;
    the detector is configured to measure second radiation proximate to the second organism over a second range of frequencies to obtain a second measured spectrum; and
    the analyzer is configured to:
    compare the second measured spectrum to a second frequency spectra signature to determine a second comparison result; and
    use the comparison result and the second comparison result to distinguish between the organism and the second organism.

17. The apparatus of claim 10, further comprising:
    a second detector,
    wherein the first detector and the second detector each measure a different frequency range.

18. A tangible computer-readable medium having stored thereon computer-executable instructions that, upon execution by a computing device, cause the computing device to perform operations comprising:

applying electromagnetic radiation to at least partially penetrate an organism using a source of the electromagnetic radiation spaced from the organism;

measuring radiation proximate to the organism over a range of frequencies to obtain a measured spectrum;

comparing the measured spectrum to a frequency spectra signature to generate a comparison result; and producing a spectrogram from the measured spectrum.

19. The tangible computer-readable medium of claim 18, wherein upon execution of the instructions by the computing device, cause the computing device to perform operations further comprising:

comparing the measured spectrum to a second frequency spectra signature to determine a second comparison result; and determining which of the frequency spectra signature and the second frequency spectra signature most closely resembles the measured spectrum.

20. The tangible computer-readable medium of claim 18, wherein upon execution of the instructions by the computing device, cause the computing device to perform operations further comprising:

applying second radiation to a second organism;

measuring second radiation proximate to the second organism over a second range of frequencies to obtain a second measured spectrum;

comparing the second measured spectrum to a second frequency spectra signature to determine a second comparison result; and using the comparison result and the second comparison result to distinguish the organism from the second organism.

21. The tangible computer-readable medium of claim 18, wherein upon execution of the instructions by the computing device, cause the computing device to perform operations further comprising:

focusing radiation on the detector.

22. The tangible computer-readable medium of claim 18, wherein upon execution of the instructions by the computing device, cause the computing device to perform operations further comprising:

measuring with a plurality of detectors.

23. The tangible computer-readable medium of claim 22, wherein each detector in the plurality of detectors measures a different frequency range.

24. A method, comprising:

applying radiation to an organism;

measuring radiation proximate to the organism over a range of frequencies between about 10 GHz and about 1 THz to obtain a measured spectrum;

comparing the measured spectrum to a frequency spectra signature to generate a comparison result; and producing a spectrogram from the measured spectrum.

25. An apparatus, comprising:

a transmitter configured to apply radiation to an organism;

a detector located proximate to the organism and configured to measure radiation that has interacted with the organism;

an apparatus configured to focus the radiation after it has interacted with the organism onto the detector; and an analyzer coupled to the detector and the transmitter, wherein the analyzer is configured to produce a measured spectrum from a detector measurement over a range of frequencies between about 10 GHz and about 1 THz and to compare the measured spectrum to a frequency spectra signature to determine a comparison result, and wherein the analyzer is configured to produce a spectrogram from the measured spectrum.

26. A tangible computer-readable medium having stored thereon computer-executable instructions that, upon execution by a computing device, cause the computing device to perform operations comprising:

applying radiation to an organism;

measuring radiation proximate to the organism over a range of frequencies between about 10 GHz and about 1 THz to obtain a measured spectrum;

comparing the measured spectrum to a frequency spectra signature to generate a comparison result; and producing a spectrogram from the measured spectrum.

* * * * *